United States Patent [19]
deSolms et al.

[11] Patent Number: 5,439,918
[45] Date of Patent: Aug. 8, 1995

[54] INHIBITORS OF FARNESYL-PROTEIN TRANSFERASE

[75] Inventors: S. Jane deSolms, Norristown; Samuel L. Graham, Schwenksville, both of Pa.

[73] Assignee: Merck & Co., Inc., Rahway, N.J.

[21] Appl. No.: 212,489

[22] Filed: Mar. 14, 1994

[51] Int. Cl.$^6$ .......................................... C07D 217/12
[52] U.S. Cl. .................... 514/307; 514/212; 514/315; 514/419; 514/423; 540/608; 546/147; 546/245; 548/492; 548/531; 548/536
[58] Field of Search .............. 546/147, 245; 548/567, 548/492, 531, 536; 514/307, 315, 428, 212, 419, 423; 540/608

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |

FOREIGN PATENT DOCUMENTS

| | | | |
|---|---|---|---|
| 0456180A1 | 11/1991 | European Pat. Off. | 435/15 |
| 0618221A2 | 10/1994 | European Pat. Off. | 514/307 |
| 91/16340 | 10/1991 | WIPO | 435/15 |

OTHER PUBLICATIONS

Kohl, N. E. et al., "Protein farnesyltransferase inhibitors block the growth of ras-dependent tumors in nude mice", Proc. Natl. Acad. Sci. USA, vol. 91, pp. 9141–9145 (1994).

Gibbs, J. B. et al., Selective Inhibition of Farnesyl–Protein Transferase Blocks Ras Processing in Vivo, (1993), The Journal of Biol. Chemistry, 268, No. 11, pp. 7617–7620.

Goldstein, J. S., et al. Journal of Biological Chemistry, vol. 266, No. 24, pp. 15575–15578 (1991).

James, G. L. et al., Benzodiazepine Peptidomimetics: Potent Inhibitors of Ras Farnesylation in Animal Cells, (1993), Science, 260, pp. 1937–1942.

Kohl, N. E. et al., Selective Inhibition of ras-Dependent Transformation by a Farnesyltransferase Inhibitor, (1993), Science, 260, pp. 1934–1937.

Leftheris, K. et al., Peptide Based P21RAS Farnesyl Transferase Inhibitors: Systematic Modification of the Tetrapepttide CA1A2X Motif, (1994), Bioorganic & Medicinal Chemistry Letters, 4, No. 7, pp. 887–892.

Pompliano, D. L. et al., Steady-State Kinetic Mechanism of Ras Farnesyl: Protein Transferase, (1992), Biochemistry, 31, pp. 3800–3807.

Qian, Y. et al., Design and Structural Requirements of Potent Peptidomimetic Inhibitors of p21ras Farnesyltransferase, (1994), The Journal of Biological Chemistry, 269, No. 17, pp. 12410–12413.

Reiss, Y. et al., Inhibition of Purified p21ras Farnesyl: Protein Transferase by Cys-AAX Tetrapeptides, (1990), Cell, 62, pp. 81–88.

Reiss, Y. et al., Sequence requirement for peptide recognition by rat brain p21 ras protein farnesyltransferase, (1991), Proc. Natl. Acad. Sci. USA, 88, pp. 732–736.

Schaber, M. D. et al., Polyisoprenylation of Ras in Vitro by a Farnesyl-Protein Transferase, (1990), The Journal of Biological Chemistry, 265, No. 25, pp. 14701–14704.

*Primary Examiner*—C. Warren Ivy
*Assistant Examiner*—Zinna N. Davis
*Attorney, Agent, or Firm*—David A. Muthard; Mark R. Daniel; Joseph F. DiPrima

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and treatment of cancer.

13 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa[1]-Aaa[2]-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989)); Hancock et al., *Cell* 57: 1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J.Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81-88 (1990); Schaber et al., *J. Biol. Chem.*, 265:14704-14704 (1990); Schafer et al., *Science*, 249: 1133-1139 (1990); Manne et al., *Proc. Natl. Acad. Sci USA*, 87:7541-7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa[1]-Aaa[2]-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634 (1989)). Cytosol localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of Ras, and other cellular proteins, with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732-736 (1991)). It was, however, disclosed that tetrapeptides which further contained a cyclic amino acid residue, such as proline, had greatly reduced inhibitory activity when compared to tetrapeptides not containing a cyclic amino acid (Reiss et al., (1991). Tetrapeptide inhibitors may inhibit while serving as alternate substrates for the Ras farnesyl-transferase enzyme, or may be purely competitive inhibitors (U.S. Pat. No. 5,141,851, University of Texas).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes partially reduced tetrapeptide analogs containing a cyclic amino acid which inhibit farnesyl-protein transferase (FPTase) and the farnesylation of the oncogene protein Ras, chemotherapeutic compositions containing the compounds of this invention, and methods for producing the compounds of this invention. It has been surprisingly found that these analogs containing a cyclic amino acid show FPTase inhibitory activity which is comparable to partially reduced tetrapeptide analogs which do not contain a cyclic amino acid. The invention also includes ester and lactone analogs which are prodrugs which deliver the active acid forms of the compounds to the intracellular compartment.

The compounds of this invention are illustrated by the formulae I and II:

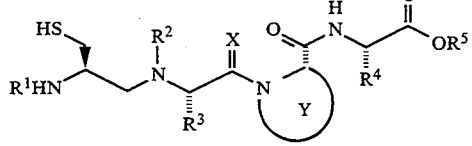

I

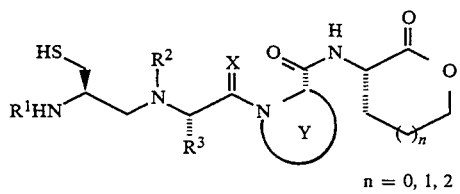

II n = 0, 1, 2

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

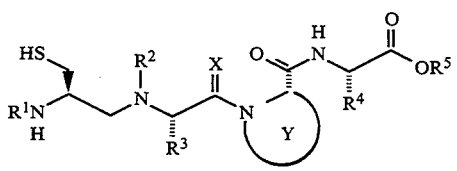

I wherein:

$R^1$ and $R^2$ are independently selected from H; $C_{1-4}$ alkyl, $C_{1-4}$ aralkyl, —S(O)$_m$—$R^6$ and

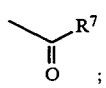

;

$R^3$ and $R^4$ are independently selected from: H; $C_{1-8}$ alkyl, alkenyl, alkynyl, or

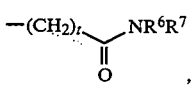

unsubstituted or substituted with one or more of:
1) aryl or heterocycle, unsubstituted or substituted with:
   a) $C_{1-4}$ alkyl,
   b) (CH$_2$)$_t$OR$^6$,
   c) (CH$_2$)$_t$NR$^6$R$^7$, or
   d) halogen,
2) $C_{3-6}$ cycloalkyl,
3) OR$^6$,
4) SR$^6$, S(O)R$^6$, SO$_2$R$^6$,

5) —NR$^6$R$^7$,

6) 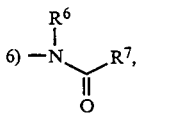

7) 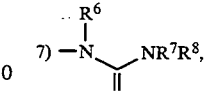

8) 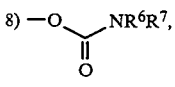

9) 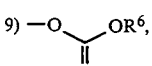

10) 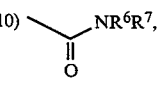

11) 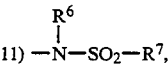

12) 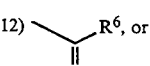, or

13) 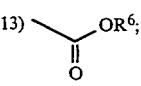;

$R^5$ is hydrogen;
$R^6$, $R^7$ and $R^8$ are independently selected from: H; $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e) 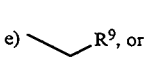, or f) —SO$_2$R$^9$, wherein
$R^6$ and $R^7$ may be joined in a ring, and
$R^7$ and $R^8$ may be joined in a ring;
$R^9$ is $C_{1-4}$ alkyl or aralkyl;
m is 0, 1 or 2;
t is 1 to 4;
X is O or H$_2$;
Y is substituted or unsubstituted nitrogen containing $C_4$–$C_9$ mono or bicyclic ring system wherein the non-nitrogen containing ring may be an aromatic ring, a $C_5$–$C_7$ saturated ring or a heterocycle, and wherein the substituent is selected from $C_{1-4}$ alkyl, $C_{3-6}$ cycloalkyl, heterocycle, aryl, said substituent which is unsubstituted or substituted with:
  a) $C_{1-4}$ alkoxy,
  b) aryl or heterocycle,
  c) halogen,
  d) HO, e) 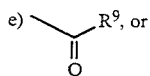, or f) —SO$_2$R$^9$;

or the pharmaceutically acceptable salts or disulfides thereof.

In a second embodiment of this invention are prodrugs of the inhibitors of farnesyl-protein transferase, those prodrugs which are illustrated by the formula I:

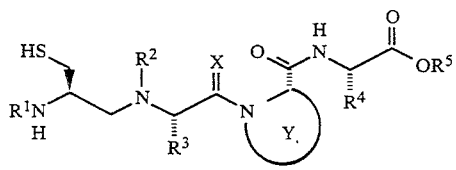

wherein:

R$^1$ and R$^2$ are independently selected from H, C$_{1-4}$ alkyl, C$_{1-4}$ aralkyl, —S(O)$_m$—R$^6$ and

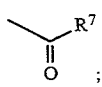 ;

R$^3$ and R$^4$ are independently selected from: H; C$_{1-8}$ alkyl, alkenyl, alkynyl, or

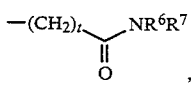 , unsubstituted or substituted with one or more of:
1) aryl or heterocycle, unsubstituted or substituted with:
  a) C$_{1-4}$ alkyl,
  b) (CH$_2$)$_t$OR$^6$,
  c) (CH$_2$)$_t$NR$^6$R$^7$,
  d) halogen,
2) C$_{3-6}$ cycloalkyl,
3) OR$^6$,
4) SR$^6$, S(O)R$^6$, SO$_2$R$^6$,

5) —NR$^6$R$^7$,

6) 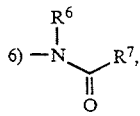

7) 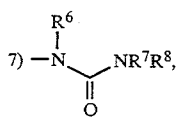

8) 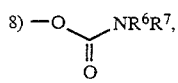

9) 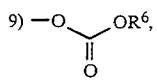

10) 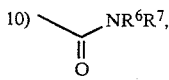,

11) 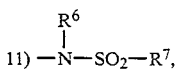,

12) 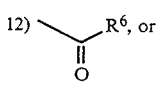, or

13) 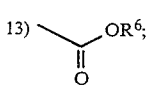;

R$^5$ is C$_{1-8}$ alkyl, C$_{3-6}$ cycloalkyl, heterocycle or aryl, unsubstituted or substituted with:
  a) C$_{1-4}$ alkoxy,
  b) aryl or heterocycle,
  c) halogen, e) 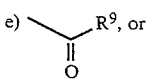, or f) —SO$_2$R$^9$;

R$^6$, R$^7$ and R$^8$ are independently selected from: H; C$_{1-4}$ alkyl, C$_{3-6}$ cycloalkyl, heterocycle, aryl, unsubstituted or substituted with:
  a) C$_{1-4}$ alkoxy,
  b) aryl or heterocycle,
  c) halogen,
  d) HO, e) , or f) —SO$_2$R$^9$, R$^6$ and R$^7$ may be joined in a ring, and
R$^7$ and R$^8$ may be joined in a ring;
R$^9$ is C$_{1-4}$ alkyl or aralkyl;
m is 0, 1 or 2;
t is 1 to 4;
X is O or H$_2$;
Y is substituted or unsubstituted nitrogen containing C$_4$–C$_9$ mono or bicyclic ring system wherein the non-nitrogen containing ring may be an aromatic ring, a C$_5$–C$_7$ saturated ring or a heterocycle, and wherein the substituent is selected from C$_{1-4}$ alkyl, C$_{3-6}$ cycloalkyl, heterocycle, aryl, said substituent which is unsubstituted or substituted with:
  a) C$_{1-4}$ alkoxy,
  b) aryl or heterocycle,
  c) halogen,
  d) HO, e) 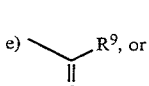, or f) —SO$_2$R$^9$;

or the pharmaceutically acceptable salts or disulfides thereof.

In a third embodiment of this invention are prodrugs of the inhibitors of farnesyl-protein transferase, those prodrugs which are illustrated by the formula II:

II wherein:
R$^1$ and R$^2$ are independently selected from H, C$_{1-4}$ alkyl, C$_{1-4}$ aralkyl, —S(O)$_m$—R$^6$ and R$^3$ is H; C$_{1-8}$ alkyl, alkenyl, alkynyl, or —(CH$_2$)$_t$—C(O)NR$^6$R$^7$, unsubstituted or substituted with one or more of:
1) aryl or heterocycle, unsubstituted or substituted with:
   a) C$_{1-4}$ alkyl,
   b) (CH$_2$)$_t$OR$^6$,
   c) (CH$_2$)$_t$NR$^6$R$^7$,
   d) halogen,
2) C$_{3-6}$ cycloalkyl,
3) OR$^6$,
4) SR$^6$, S(O)R$^6$, SO$^2$R$^6$,
5) —NR$^6$R$^7$,
6) —N(R$^6$)C(O)R$^7$,
7) —N(R$^6$)C(O)NR$^7$R$^8$,
8) —OC(O)NR$^6$R$^7$,
9) —OC(O)OR$^6$,
10) —C(O)NR$^6$R$^7$,
11) —N(R$^6$)—SO$_2$—R$^7$,
12) —C(O)R$^6$, or

13) —C(O)OR$^6$;

R$^6$, R$^7$ and R$^8$ are independently selected from: H; C$_{1-4}$ alkyl, C$_{3-6}$ cycloalkyl, heterocycle, aryl, unsubstituted or substituted with:
a) C$_{1-4}$ alkoxy,
b) aryl or heterocycle,
c) halogen,
d) HO, e) —C(O)R$^9$, or f) —SO$_2$R$^9$, wherein
R$^6$ and R$^7$ may be joined in a ring, and
R$^7$ and R$^8$ may be joined in a ring;
R$^9$ is C$_{1-4}$ alkyl or aralkyl;
m is 0, 1 or 2;
n is 0, 1 or 2;
t is 1 to 4;
X is O or H$_2$;
Y is substituted or unsubstituted nitrogen containing C$_4$–C$_9$ mono or bicyclic ring system wherein the non-nitrogen containing ring may be an aromatic ring, a C$_5$–C$_7$ saturated ring or a heterocycle, and wherein the substituent is selected from C$_{1-4}$ alkyl, C$_{3-6}$ cycloalkyl, heterocycle, aryl, said substituent which is unsubstituted or substituted with:
a) C$_{1-4}$ alkoxy,
b) aryl or heterocycle,
c) halogen,
d) HO, e) —C(O)R$^9$, or f) —SO$_2$R$^9$;

or the pharmaceutically acceptable salts or disulfides thereof.

In a preferred embodiment of this invention, the inhibitors of farnesyl-protein transferase are illustrated by the formula I:

I wherein
R$^1$ and R$^2$ are independently selected from H and C$_{1-4}$ alkyl;
R$^3$ and R$^4$ are independently selected from: H; C$_{1-8}$ alkyl, alkenyl,
alkynyl, or

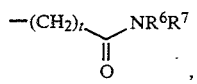

unsubstituted or substituted with one or more of:
1) aryl or heterocycle, unsubstituted or substituted with:
   a) $C_{1-4}$ alkyl,
   b) $(CH_2)_tOR^6$,
   c) $(CH_2)_tNR^6R^7$,
   d) halogen,
2) $C_{3-6}$ cycloalkyl,
3) $OR^6$,
4) $SR^6$, $S(O)R^6$, $SO_2R^6$,
$R^5$ is hydrogen;
$R^6$, $R^7$ and $R^8$ are independently selected from: H; $C_{1-4}$ alkyl, $C_{3-6}$ cycloalkyl, heterocycle, aryl, unsubstituted or substituted with:
   a) $C_{1-4}$ alkoxy,
   b) aryl or heterocycle,
   c) halogen,
   d) HO, e) 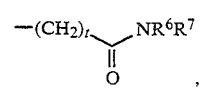  or f) $-SO_2R^9$, wherein
$R^6$ and $R^7$ may be joined in a ring, and
$R^7$ and $R^8$ may be joined in a ring;
$R^9$ is $C_{1-4}$ alkyl or aralkyl;
m is 0, 1 or 2;
t is 1 to 4;
X is $H_2$;
Y is substituted or unsubstituted ring system selected from the following

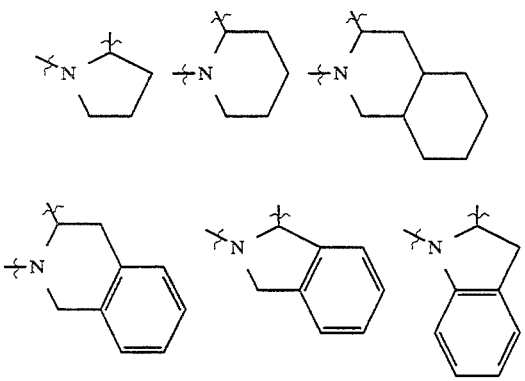

and wherein the substituent is selected from $C_{1-4}$ alkyl, $C_{3-6}$ cycloalkyl, heterocycle, aryl, said substituent which is unsubstituted or substituted with:
   a) $C_{1-4}$ alkoxy,
   b) aryl or heterocycle,
   c) halogen,
   d) HO, e) ⧹―C(=O)R⁹, or f) $-SO_2R^9$;

or the pharmaceutically acceptable salts or disulfides thereof.

In another preferred embodiment of this invention are prodrugs of the inhibitors of farnesyl-protein transferase, those prodrugs which are illustrated by the formula I:

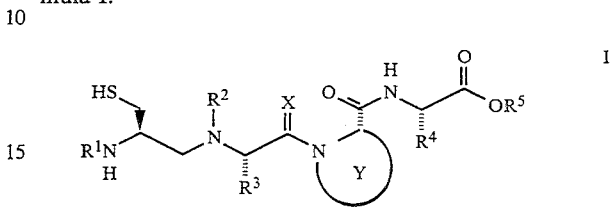

wherein:
$R^1$ and $R^2$ are independently selected from H and $C_{1-4}$ alkyl;
$R^3$ and $R^4$ are independently selected from: H; $C_{1-8}$ alkyl, alkenyl, alkynyl, or ―(CH₂)_t―C(=O)NR⁶R⁷, unsubstituted or substituted with one or more of:
1) aryl or heterocycle, unsubstituted or substituted with:
   a) $C_{1-4}$ alkyl,
   b) $(CH_2)_tOR^6$,
   c) $(CH_2)_tNR^6R^7$,
   d) halogen,
2) $C_{3-6}$ cycloalkyl,
3) $OR^6$,
4) $SR^6$, $S(O)R^6$, $SO_2R^6$, $R^5$ is $C_{1-8}$ alkyl, $C_{3-6}$ cycloalkyl, heterocycle or aryl, unsubstituted or substituted with:
   a) $C_{1-4}$ alkoxy,
   b) aryl or heterocycle,
   c) halogen,
   d) HO, e) ⧹―C(=O)R⁹, or f) $-SO_2R^9$;

$R^6$, $R^7$ and $R^8$ are independently selected from: H; $C_{1-4}$ alkyl, $C_{3-6}$ cycloalkyl, heterocycle, aryl, unsubstituted or substituted with:
   a) $C_{1-4}$ alkoxy,
   b) aryl or heterocycle,
   c) halogen,
   d) HO, e) ⧹―C(=O)R⁹, or f) $-SO_2R^9$, wherein
$R^6$ and $R^7$ may be joined in a ring, and
$R^7$ and $R^8$ may be joined in a ring;

$R^9$ is $C_{1-4}$ alkyl or aralkyl;
m is 0, 1 or 2;
t is 1 to 4;
X is $H_2$;
Y is substituted or unsubstituted ring system selected from the following wherein the substituent is selected from $C_{1-4}$ alkyl, $C_{3-6}$ cycloalkyl, heterocycle, aryl, said substituent which is unsubstituted or substituted with:
 a) $C_{1-4}$ alkoxy,
 b) aryl or heterocycle,
 c) halogen,
 d) HO, e) $\overset{\displaystyle R^9}{\underset{O}{\|}}$, or f) $-SO_2R^9$;

or the pharmaceutically acceptable salts or disulfides thereof.

In another preferred embodiment of this invention are prodrugs of the inhibitors of farnesyl-protein transferase, those prodrugs which are illustrated by the formula II:

II wherein:
$R^1$ and $R^2$ are independently selected from H, $C_{1-4}$ alkyl, $C_{1-4}$ aralkyl, $-S(O)_m-R^6$ and $\overset{\displaystyle R^7}{\underset{O}{\|}}$ ;

$R^3$ and $R^4$ are independently selected from: H; $C_{1-8}$ alkyl, alkenyl, alkynyl, or $-(CH_2)_t \overset{\displaystyle NR^6R^7}{\underset{O}{\|}}$ , unsubstituted or substituted with one or more of:
 1) aryl or heterocycle, unsubstituted or substituted with:
  a) $C_{1-4}$ alkyl,
  b) $(CH_2)_tOR^6$,
  c) $(CH_2)_tNR^6R^7$,
  d) halogen,
 2) $C_{3-6}$ cycloalkyl,
 3) $OR^6$,
 4) $SR^6$, $S(O)R^6$, $SO_2R^6$,
$R^5$ is $C_{1-8}$ alkyl, $C_{3-6}$ cycloalkyl, heterocycle or aryl, unsubstituted or substituted with:
 a) $C_{1-4}$ alkoxy,
 b) aryl or heterocycle,
 c) halogen,
 d) HO, e) $\overset{\displaystyle R^9}{\underset{O}{\|}}$, or f) $-SO_2R^9$;

$R^6$, $R^7$ and $R^8$ are independently selected from: H; $C_{1-4}$ alkyl, $C_{3-6}$ cycloalkyl, heterocycle, aryl, unsubstituted or substituted with:
 a) $C_{1-4}$ alkoxy,
 b) aryl or heterocycle,
 c) halogen,
 d) HO, e) $\overset{\displaystyle R^9}{\underset{O}{\|}}$, or f) $-SO_2R^9$, wherein
$R^6$ and $R^7$ may be joined in a ring, and
$R^7$ and $R^8$ may be joined in a ring;
$R^9$ is $C_{1-4}$ alkyl or aralkyl;
m is 0, 1 or 2;
n is 0, 1 or 2;
t is 1 to 4;
X is $H_2$;
Y is substituted or unsubstituted ring system selected from the following wherein the substituent is selected from $C_{1-4}$ alkyl, $C_{3-6}$ cycloalkyl, heterocycle, aryl, said substituent which is unsubstituted or substituted with:
a) $C_{1-4}$ alkoxy,
b) aryl or heterocycle,
c) halogen,
d) HO, e) 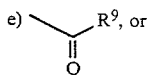

f) $-SO_2R^9$;

or the pharmaceutically acceptable salts or disulfides thereof.

Specific compounds of this invention are as follows:
N-[N'-[2(S)-(2(R)-amino-3-mercaptopropylamino)-3(S)-methylpentyl]-1,2,3,4-tetrahydro-3(S)-isoquinolinecarboxyl]-methionine methyl ester (Compound 1)
N-[N'-[2(S)-(2(R)-amino-3-mercaptopropylamino)-3(S)-methylpentyl]-1,2,3,4-tetrahydro-3(S)-isoquinolinecarboxyl]-methionine (Compound 2)
N-[2(S)-(2(R)-amino-3-mercaptopropylamino)-3(S)-methylpentyl]-prolyl-methionine methyl ester (Compound 3)
N-[2(S)-(2(R)-amino-3-mercaptopropylamino)-3(S)-methylpentyl]-prolyl-methionine (Compound 4)
N-[2(S)-(2(R)-amino-3-mercaptopropylamino)-3(S)-methylpentyl]-trans-3-ethyl-prolyl-methionine methyl ester (Compound 5)
N-[2(S)-(2(R)-amino-3-mercaptopropylamino)-3(S)-methylpentyl]-trans-3-ethyl-prolyl-methionine (Compound 6)
N-[2(S)-(2(R)-amino-3-mercaptopropylamino)-3(S)-methylpentyl]-cis-3-ethyl-prolyl-methionine methyl ester (Compound 7)
N-[2(S)-(2(R)-amino-3-mercaptopropylamino)-3(S)-methylpentyl]-cis-3-ethyl-prolyl-methionine (Compound 8)
N-[2(S)-(2(R)-amino-3-mercaptopropylamino)-3(S)-methylpentyl]-prolyl-methionine sulfone methyl ester (Compound 9)
N-[2(S)-(2(R)-amino-3-mercaptopropylamino)-3(S)-methylpentyl]-prolyl-methionine sulfone (Compound 10)
N-[2(S)-(2(R)-amino-3-mercaptopropylamino)-3-methylpentyl]-2(S)-pipecolyl-methionine methyl ester (Compound 11)
N-[2(S)-(2(R)-amino-3-mercaptopropylamino)-3-methylpentyl]-2(S)-pipecolyl-methionine (Compound 12)
N-[N'-[2(S)-(2(R)-amino-3-mercaptopropylamino)-3(S)-methylpentyl]-1,2,3,4-tetrahydro-3(S)-isoquinolinecarboxyl]-homoserine lactone (Compound 13)
N-[N'-[2(S)-(2(R)-amino-3-mercaptopropylamino)-3(S)-methylpentyl]-1,2,3,4-tetrahydro-3(S)-isoquinolinecarboxyl]-homoserine (Compound 14)
N-[2(S)-(2(R)-amino-3-mercaptopropylamino)-3(S)-methylpentyl]-prolyl-homoserine lactone (Compound 15)
N-[2(S)-(2(R)-amino-3-mercaptopropylamino)-3(S)-methylpentyl]-prolyl-homoserine (Compound 16)
N-[2(S)-(2(R)-amino-3-mercaptopropylamino)-3-methylpentyl]-2(S)-pipecolyl-homoserine lactone (Compound 17)
N-[2(S)-(2(R)-amino-3-mercaptopropylamino)-3-methylpentyl]-2(S)-pipecolyl-homoserine (Compound 18)
N-[2(R)-amino-3-mercaptopropyl]-isoleucyl-prolyl-homserine lactone (Compound 19)
N-[2(R)-amino-3-mercaptopropyl]-isoleucyl-prolyl-homserine (Compound 20)
N-[2(R)-amino-3-mercaptopropyl]-isoleucyl-2(S)-pipecolyl-homserine lactone (Compound 21)
N-[2(R)-amino-3-mercaptopropyl]-isoleucyl-2(S)-pipecolyl-homserine (Compound 22)
N-[2(S)-(2(R)-amino-3-(mercaptopropyl)methylamino)-3(S)-methylpentyl]-prolyl-methionine methyl ester (Compound 23)
N-[2(S)-(2(R)-amino-3-(mercaptopropyl)methylamino)-3(S)-methylpentyl]-prolyl-methionine (Compound 24)
N-[2(S)-(2(R)-amino-3-(mercaptopropyl)methylamino)-3(S)-methylpentyl]-prolyl-methionine sulfone methyl ester (Compound 25) and
N-[2(S)-(2(R)-amino-3-(mercaptopropyl)methylamino)-3(S)-methylpentyl]-prolyl-methionine sulfone (Compound 26)

or the pharmaceutically acceptable salts or disulfides thereof.

The preferred compounds of this invention include the following inhibitor and the corresponding lactone/-ester prodrug pairs:

N-[N'-[2(S)-(2(R)-amino-3-mercaptopropylamino)-3(S)-methylpentyl]-1,2,3,4-tetrahydro-3(S)-isoquinolinecarboxyl]-homoserine (Compound 14) and N-[N'-[2(S)-(2(R)-amino-3-mercaptopropylamino)-3(S)-methylpentyl]-1,2,3,4-tetrahydro-3(S)-isoquinolinecarboxyl]-homoserine lactone (Compound 13)

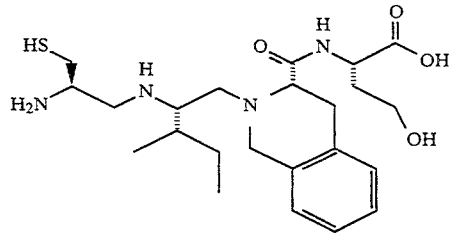

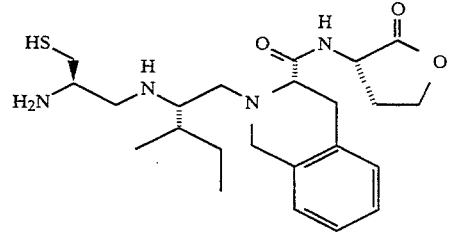

N-[N'-[2(S)-(2(R)-amino-3-mercaptopropylamino)-3(S)-methylpentyl]-1,2,3,4-tetrahydro-3(S)-isoquinolinecarboxyl]-methionine (Compound 2) and
N-[N'-[2(S)-(2(R)-amino-3-mercaptopropylamino)-3(S)-methylpentyl]-1,2,3,4-tetrahydro-3(S)-isoquinolinecarboxyl]-methionine methyl ester (Compound 1)

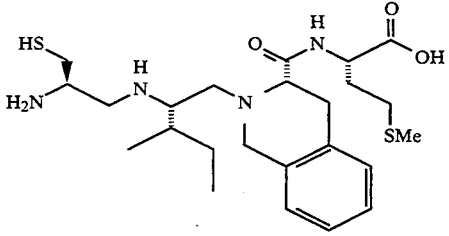

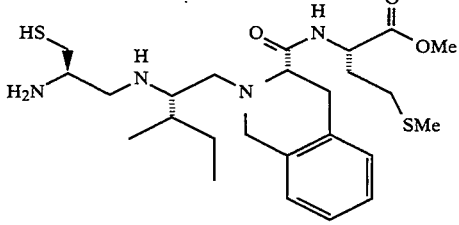

N-[2(S)-(2(R)-amino-3-mercaptopropylamino)-3(S)-methylpentyl]-trans-3-ethyl-prolyl-methionine methyl ester (Compound 5) and N-[2(S)-(2(R)-amino-3-mercaptopropylamino)-3(S)-methylpentyl]-trans-3-ethyl-prolyl-methionine (Compound 6)

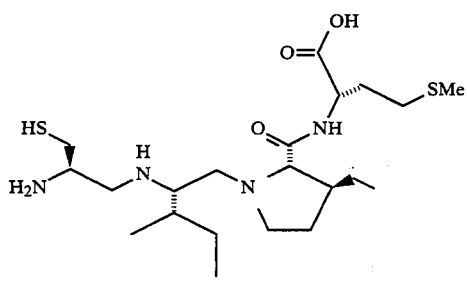

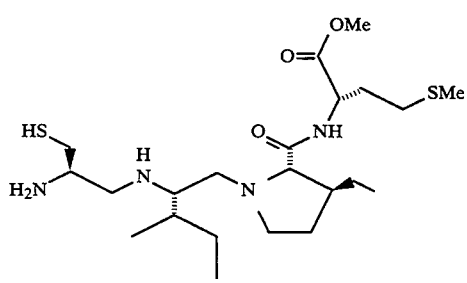

The compounds of the present invention may have asymmetric centers and occur as racemates, racemic mixtures, and as individual diastereomers, with all possible isomers, including optical isomers, being included in the present invention. The present invention further includes all disulfides of the claimed compounds, derived from two of the same compounds. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and $S(O)_m$ (wherein m=0, 1 or 2), and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, the phrase "nitrogen containing $C_4$–$C_9$ mono or bicyclic ring system wherein the non-nitrogen containing ring may be a $C_6$ aromatic ring" which defines moiety "Y" of the instant invention includes but is not limited to the following ring systems:

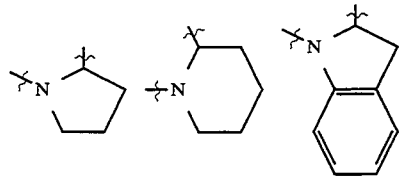

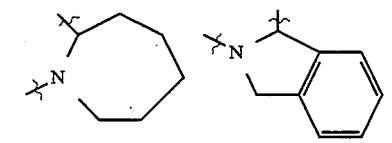

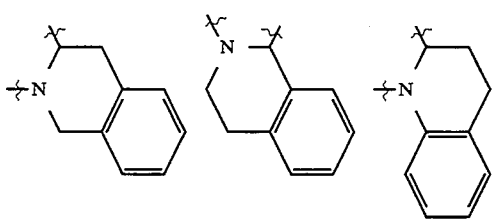

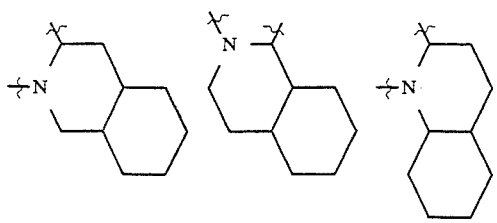

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:
Ac₂O Acetic anhydride;
Boc t-Butoxycarbonyl;
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimide hydrochloride;
HOBT 1-Hydroxybenzotriazole hydrate;
Et₃N Triethylamine;
EtOAc Ethyl acetate.
FAB Fast atom bombardment;
HOOBT 3-Hydroxy-1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide
Py Pyridine;
TFA Trifluoroacetic acid;
THF Tetrahydrofuran;

The compounds of this invention are prepared by employing reactions A–C as shown in the Reaction Scheme, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

These reactions may be employed in a linear sequence to provide the compounds of the invention or they may be used to synthesize fragments which are subsequently joined by the alkylation reactions described in the Reaction Schemes.

REACTION SCHEME A

Reaction A. Coupling of residues to form an amide bond

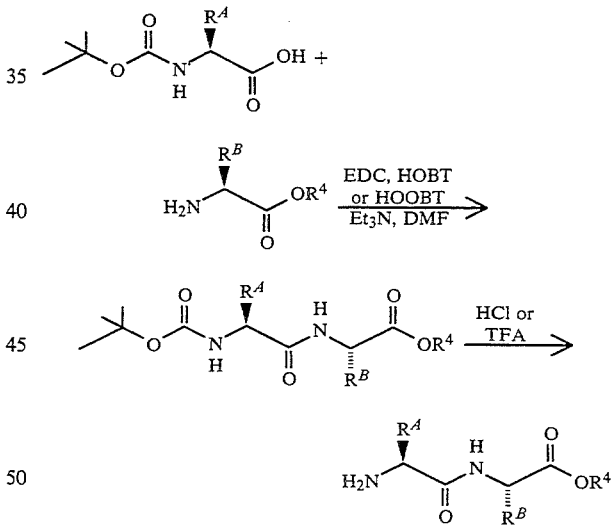

REACTION SCHEME B

Reaction B. Preparation of reduced peptide subunits by reductive alkylation

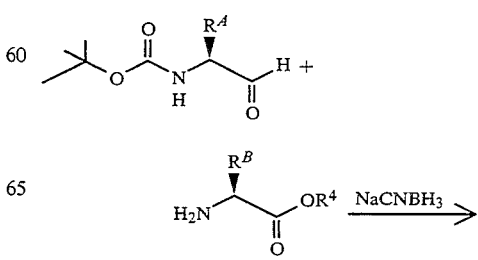

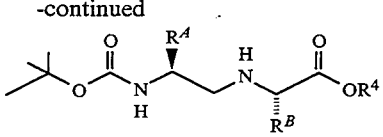

REACTION SCHEME C

Reaction C. Alkylation/reductive alkylation of reduced peptide subunits

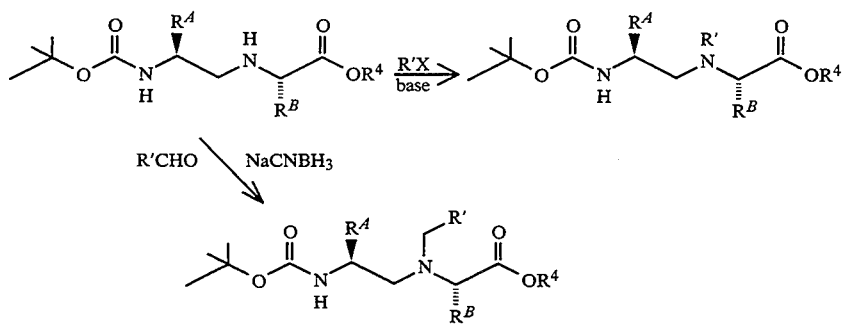

where $R^A$ and $R^B$ are $R^3$, $R^4$ or part of the structure of Y as previously defined, including their protected forms compatible with the reaction conditions shown, for example, the triphenylmethyl (trityl) protected side chain of cysteine.

The compounds of this invention inhibit farnesyl-protein transferase and the farnesylation of the onco-gene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof. Purification by HPLC was accomplished with a 40×100 mm Waters Prep-Pak® reverse phase HPLC column (Delta-Pak ™ $C_{18}$ 15 μm, 100 Å). Gradient elution employed 0.1% trifluoroacetic acid in water (Solvent A) and 0.1% trifluoroacetic acid in acetonitrile (Solvent B). Chloride salts were obtained by passing an aqueous solution of the trifluoroacetic acid salt through a Biorad AG® 3×4 ion exchange resin column (100–200 mesh, Cl-form). Purification by HPLC was utilized for each of the Examples 1–5, Compounds 1–26, as set forth below.

Example 1

Preparation of N-[N'-[2(S)-(2(R)-Amino-3-mercaptopropylamino)-3(S)-methylpentyl]-1,2,3,4-tetrahydro-3(S)-isoquinolinecarboxyl]-methionine methyl ester (Compound 1)

Step A. N-(t-butoxycarbonyl)-isoleucine aldehyde.

This compound was synthesized by applying the procedure of Goel, Krolls, Stier, and Kesten to N-(t-butoxycarbonyl)-isoleucine. The compound was obtained as a colorless oil, which was used without purification.

Step B. N-[(2S)-(t-Butoxycarbonylamino)-3(S)-methylpentyl)-1,2,3,4-tetrahydro-3(S)-isoquinolinecarboxylic acid benzyl ester.

N-(t-Butoxycarbonyl)-isoleucine aldehyde (1.5 g, 0.0070 mol) and 1,2,3,4-tetrahydro-3(S)-isoquinolinecarboxylic acid benzyl ester (2.23 g, 0.0084 mol) were dissolved in MeOH (30 mL) at ambient temperature under nitrogen and treated with 3A molecular sieves (3 g) and sodium cyanoborohydride (0.66 g, 0.0105 mol) with stirring. After 18 h the mixture was filtered, concentrated, and the residue was partitioned between EtOAc (50 mL) and saturated aqueous NaHCO$_3$ solution (50 mL). The basic layer was washed with EtOAc (3×30 mL), the organics combined, washed with brine, and dried (Na$_2$SO$_4$). Filtration and concentration to dryness gave the title compound as a colorless oil after chromatography (SiO$_2$, hexane: EtOAc, 6:1).

$^1$H NMR (CDCl$_3$) δ7.35–7.02 (m, 9H), 5.11 (s, 2H), 4.78–4.6 (m, 1H), 3.98 (s, 2H), 3.84 (t, 1H, J=5 Hz), 3.75–3.64 (m, 1H), 3.27–3.05 (m, 2H), 2.84 (dd, 1 H, J=5, 13 Hz), 2.59 (dd, 1 H, J=5, 13 Hz), 1.82–1.70 (m, 1H), 1.40 (s, 9H), 1.37–1.26 (m, 1H), 1.13–0.97 (m, 1H), 0.92 (d,3 H, J=7 Hz), 0.86 (t, 3H, J=7 Hz).

Step C. N-[(2S)-(t-Butoxycarbonylamino)-3(S)-methylpentyl)-1,2,3,4-tetrahydro-3(S)-isoquinolinecarboxylic acid.

N-[(2S )-(t-Butoxycarbonylamino)-3(S)-methylpentyl)-1,2,3,4-tetrahydro-3(S)-isoquinolinecarboxylic acid benzyl ester (1.5 g, 0.0032 mol) was dissolved in methanol (50 mL) - EtOAc (50 mL), treated with 10% palladium on carbon (0.15 g) and hydrogenated under a balloon of hydrogen for 4 h. Filtration and concentration to dryness gave the title compound as a white solid which was used without further purification.

Step D. N-[2(S)-(t-butoxycarbonylamino-3(S)-methylpentyl]-1,2,3,4-tetrahydro-3(S)-isoquinolinecarboxyl-methionine methyl ester.

N-[(2S)-(t-Butoxycarbonylamino)-3(S)-methylpentyl)- 1,2,3,4-tetrahydro-3(S)-isoquinolinecarboxylic acid (0.67 g, 0.00178 mol) was dissolved in DMF (10 mL) with stirring at ambient temperature and treated with EDC (0.376 g, 0.00196 mol), HOBT (0.265 g, 0.00196 mol), and methionine methyl ester hydrochloride (0.427 g, 0.00214 mol). The pH was adjusted to 7 with Et$_3$N (0.546 mL, 0.00392 mol) and stirring was continued for 18 h. The reaction mixture was concentrated, then partitioned between EtOAc (50 mL)-H$_2$O (50 mL). The aqueous layer was washed with EtOAc (2×30 mL), the organics combined, washed with aqueous saturated NaHCO$_3$ solution, brine, and dried (Na$_2$SO$_4$). Filtration and concentration gave the title compound after chromatography (SiO$_2$, CH$_2$Cl$_2$: MeOH, 99.5:0.5).

$^1$H NMR (CD$_3$OD) δ7.2–7.05 (m, 4H), 4.52–4.43 (m, 1H), 3.98 (d, 1H, J=13 Hz), 3.82–3.68 (m, 2H), 4.87 (s, 3H), 3.55 (t, 1H, J=6 Hz), 3.14–2.96 (m, 2H), 2.84 (dd, 1H, J=5, 13 Hz), 2.70 (dd, 1H, J=5,13 Hz), 2.14–1.88 (m, 2H), 1.95 (s, 3H), 1.57–1.32 (m, 2H), 1.41 (s, 9H), 1.25–1.06 (m, 1H), 0.96–0.84 (m, 6H).

Step E. N-[2(S)-amino-3(S)-methylpentyl]-1,2,3,4-tetrahydro-3(S)-isoquinolinecarboxyl-methionine methyl ester.

HCl gas was bubbled into a solution of N-[2(S)-(t-butoxycarbonylamino-3(S)-methylpentyl]-1,2,3,4-tetrahydro-3(S)-isoquinolinecarboxyl-methionine methyl ester (0.37 g, 0.71 mmol) in EtOAc (25 mL) with stirring at −20° C. over 0.5 h. The solution was purged with argon for 0.5 h, then concentrated to give the title compound as a white solid which was used without further purification.

Step F. Preparation of N-(t-butoxycarbonyl)-S-triphenylmethyl cysteine aldehyde.

This compound was synthesized by applying the procedure of Goel, Krolls, Stier, and Kesten to N-(t-butoxycarbonyl)-S-trityl cysteine. The compound was obtained as a white solid, which was used without purification.

$^1$H NMR (CDCl$_3$) δ9.2 (1H, s), 7.5–7.1 (18H, m), 5.1 (1H, br d), 3.92 (1H, m), 2.85–2.5 (2H, m), 1.4 (9H, s).

Step G. N-[N'-[2(S)-(2(R)-(t-butoxycarbonylamino)-3-triphenylmethyl mercaptopropylamino)-3(S)-methylpentyl]-1,2,3,4-tetrahydro-3(S)isoquinolinecarboxyl]-methionine methyl ester.

N-[2(S)-amino-3(S)-methylpentyl]-1,2,3,4-tetrahydro-3(S)-isoquinolinecarboxyl-methionine methyl ester (0.35 g, 0.71 mmol) was dissolved in methanol (15 mL), treated with KOAc (0.139 g, 1.42 mmol), 3A molecular sieves (0.4 g), and N-(t-butoxycarbonylamino)-S-triphenylmethylcysteine aldehyde (0.381 g, 0.852 mmol) followed by sodium cyanoborohydride (0.67 g, 1.065 mmol) and stirred at ambient temperature for 18 h. The reaction mixture was filtered and partitioned between EtOAc (20 mL) and aqueous saturated NaHCO$_3$ solution. The organic layer was washed with brine and dried (Na$_2$SO$_4$). Filtration and concentration to dryness gave a solid product which was chromatographed (SiO$_2$, hexane:EtOAc, 4:1 to 1:1) to give the title compound.

$^1$H NMR (CD$_3$OD) δ7.42–7.01 (m, 19H), 4.5–4.4 (m, 1H), 3.93 (d, 1H, J=15 Hz), 3.79 (d, 1H, J=15 Hz), 3.64 (s, 3H), 3.6–3.52 (m, 1H), 3.1–2.9 (m, 2H), 2.68–2.5 (m, 3H), 2.5–2.14 (m, 6H), 2.05–1.84 (m, 2H),1.98 (s, 3H), 1.68–1.46 (m, 2H), 1.41 (s, 9H), 1.37–1.23(m, 1H), 1.2–1.02 (m, 1H), 0.90 (t, 3H, J=7 Hz), 0.79 (d, 3H, J=7 Hz).

Step H. N-[N'-[2(S)-(2(R)-Amino-3-mercaptopropylamino)-3(S)-methylpentyl]-1,2,3,4-tetrahydro-3(S)-isoquinolinecarboxyl]-methionine methyl ester.

N-[N'-[2(S)-(2(R)-(t-butoxycarbonylamino)-3-triphenylmethyl mercaptopropylamino)-3(S)-methylpentyl]-1,2,3,4-tetrahydro-3(S)-isoquinolinecarboxyl]-methionine methyl ester (0.10 g, 0.117 mmol) was dissolved in CH$_2$Cl$_2$ (3 mL), treated with TFA (1mL) and triethylsilane (0.0.075 mL, 0.47 mmol), and stirred at ambient temperature for 2 h. The solution was concentrated to dryness and triturated with 0.1% TFA in H$_2$O. The solid triphenylmethane was removed by filtration and the filtrate was concentrated and purified by HPLC to give the title compound as its trifluoroacetate salt.

$^1$H NMR (CD$_3$OD) δ7.35–7.15 (m, 4H), 4.29 9S, 2H), 4.77–4.7 (m, 1H), 3.6 (t, 1H, J=6 Hz), 3.46–3.16 (m, 3H), 3.11–2.98 (m, 3H), 2.91 (d, 2H), J=6 Hz), 2.9–2.74 (m, 1H), 2.68–2.45 (m, 2H), 2.3–2.14 (m, 1H), 2.10 (s, 3H), 2.1–1.95 (m, 1H), 1.92–1.77 (m, 1H), 1.5–1.17 (m, 2H), 1.03–0.89 (m, 6H). Anal. Calcd for C$_{25}$H$_{42}$N$_4$O$_3$S$_2$2.5 CF$_3$CO$_2$H: C, 45.27; H, 5.64; N, 7.04. Found: C, 45.67; H, 5.74; N, 7.30. MS 511 (M+1)

Example 2

Preparation of
N-[N'-[2(S)-(2(R)-Amino-3-mercapto-
propylamino)3(S)-methylpentyl]-1,2,3,4-tetrahydro-
3(S)-isoquinolinecarboxyl]methionine (Compound 2)

Step A. N-[N'-[2(S)-(2(R)-(t-butoxycarbonylamino)-
3-triphenylmethyl mercaptopropylamino)-3(S)-methyl-
pentyl]-1,2,3,4-tetrahydro-3(S)isoquinolinecarboxyl]-
methionine N-[N'-[2(S)-(2(R)-(t-butoxycarbonylamino)-3-tri-
phenylmethyl mercaptopropylamino)-3(S)-methylpen-
tyl]-1,2,3,4-tetrahydro-3(S)isoquinolinecarboxyl]-meth-
ionine methyl ester from Example 1, Step G (0.2 g, 0.234 mmol) was dissolved in MeOH (4 mL) and 1N NaOH solution (0.94 mL, 0.94 mmol) in an ice-H$_2$O bath and stirred for 3 h. The solution was treated with 1N HCl (0.94 mL, 0.94 mmol), concentrated to remove the MeOH, and partitioned between EtOAc and H$_2$O. The organic layer was washed with brine and dried (Na$_2$SO$_4$). Filtration and concentration to dryness gave the title compound as a white solid which was used without further purification.

Step B. N-[N'-[2(S)-(2(R)-Amino-3-mercapto-
propylamino)-3(S)methylpentyl]-1,2,3,4-tetrahydro-
3(S)-isoquinolinecarboxyl]-methionine N-[N'-[2(S)-(2(R)-(t-butoxycarbonylamino)-3-tri-
phenylmethyl mercaptopropylamino)-3(S)-methylpen-
tyl]-1,2,3,4-tetrahydro-3(S)-isoquinolinecarboxyl]-
methionine (0.18 g, 0.215 mmol) was dissolved in CH$_2$Cl$_2$ (3 mL), treated with TFA (1 mL) and triethylsilane (0.137 mL, 0.858 mmol), and stirred at ambient temperature for 2 h. The reaction mixture was concentrated, the residue extracted with 0.1% TFA in H$_2$0, purified by HPLC and lyophilized to give the title compound.

$^1$H NMR (CD$_3$OD) δ7.34–7.17 (m, 4H), 4.72–4.65 (m, 1H), 4.31 (s, 2H), 4.21–4.13(m, 1H), 3.60 (t, 1H, J=6 Hz), 3.44 (dd, 1H, J=5,15 Hz), 3.3–3.13 (m, 3H), 3.04 (s, 2H), 2.92 (d, 2H, J=6 Hz), 2.91–2.74 (m, 1H), 2.70–2.46 (m, 2H), 2.33–2.14 (m, 1H), 2.10 (s, 3H), 2.09–1.98 (m, 1H), 1.90–1.75 (m, 1H), 1.45–1.15 (m, 2H), 1.01–0.84 (m, 6H). Anal. calcd for C$_{24}$H$_{40}$N$_4$O$_3$S$_2$. 3CF$_3$CO$_2$H: C,42.96; H,5.17;N, 6.68; Found: C,42.90; H, 5.54; N, 6.96.

The following compounds were prepared following the methods of Examples 1 and 2 substituting for the 1,2,3,4-tetrahydro-3(S)isoquinoline carboxylic acid benzyl ester in Example 1, Step B, either (S)-proline benzyl ester, pipecolic acid methyl ester, trans-3-ethyl-2(S)-proline methyl ester or cis-3-ethyl-2(S)-proline methyl ester:

N-[2(S)-(2(R)-amino-3-mercaptopropylamino)-3(S)-
methylpentyl]-prolyl-methionine methyl ester
(Compound 3)

Anal. calculated for C$_{20}$H$_{40}$N$_4$O$_3$S$_2$.3 HCl. 1 H$_2$O: C,41.63; H, 7.88; N, 9.71; Found: C, 41.82; H, 7.59; N, 9.32.

N-[2(S)-(2(R)-amino-3-mercaptopropylamino)-3(S)-
methylpentyl]-prolyl-methionine (Compound 4)

Anal. calculated for C$_{19}$H$_{38}$N$_4$O$_3$S$_2$.3 CF$_3$CO$_2$H: C, 38.66; H,5.32; N, 7.21; Found: C, 38.30; H, 5.36; N, 7.05.

N-[2(S)-(2(R)-amino-3-mercaptopropylamino)-3(S)-
methylpentyl]-trans-3-ethyl-prolyl-methionine methyl
ester (Compound 5)

m/e 477 (M+1)

N-[2(S)-(2(R)-amino-3-mercaptopropylamino)-3(S)-
methylpentyl]-trans-3-ethyl-prolyl-methionine
(Compound 6)

Anal. calculated for C$_{21}$H$_{42}$N$_4$O$_3$S$_2$.3.5 CF$_3$CO$_2$H: C,39.02; H,5.32; N, 6.50; Found: C, 39.26; H, 5.31; N, 6.75.

N-[2(S)-(2(R)-amino-3-mercaptopropylamino)-3(S)-
methylpentyl]-cis-3-ethyl-prolyl-methionine methyl
ester (Compound 7)

Anal. calculated for C$_{22}$H$_{44}$N$_4$O$_3$S$_2$.3 CF$_3$ co$_2$H.1.5 H$_2$O: C, 39.76; H,5.96; N, 6.62; Found: C,39.38; H, 5.58; N, 6.90.

N-[2(S)-(2(R)-amino-3-mercaptopropylamino)-3(S)-
methylpentyl]-cis3-ethyl-proly-methionine (Compound 8)

Anal. calculated for C$_{21}$H$_{42}$N$_4$O$_3$S$_2$.3 CF$_3$CO$_2$H2.5 H$_2$O: C, 38.16; H,5.93; N, 6.59; Found: C, 37.70; H, 5.36; N, 6.87.

N-[2(S)-(2(R)-amino-3-mercaptopropylamino)-3(S)-
methylpentyl]-prolyl-methionine sulfone methyl ester
(Compound 9)

Anal. calculated for C$_{20}$H$_{40}$N$_4$O$_5$S$_2$.3HCl..0.75 CH$_2$Cl$_2$: C, 38.12; H, 6.86; N, 8.57; Found: C, 38.04; H, 6.82; N, 8.23.

N-[2(S)-(2(R)-amino-3-mercaptopropylamino)-3(S)-
methylpentyl]-prolyl-methionine sulfone (Compound 10)

Anal. calculated for C$_{19}$H$_{38}$N$_4$O$_5$S$_2$.3 CF$_3$CO$_2$H. H$_2$O: C, 36.32; H, 5.24; N, 6.78; Found: C, 36.18; H, 5.28; N, 6.53.

N-[2(S)-(2(R)-amino-3-mercaptopropylamino)-3-
methylpentyl]-2(S)-pipecolyl-methionine methyl ester
(Compound 11)

Anal. calculated for C$_{21}$H$_{42}$N$_4$O$_3$ S$_2$.3CF$_3$CO$_2$H: C, 40.30; H, 5.64; N, 6.96; Found: C, 40.25; H, 5.86; N, 7.16.

N-[2(S)-(2(R)-amino-3-mercaptopropylamino)-3-
methylpentyl]-2(S)-pipecolyl-methionine (Compound 12)

Anal. calculated for C$_{20}$H$_{40}$N$_4$O$_3$S$_2$.3CF$_3$CO$_2$H.0.75 H$_2$O: C, 38.82; H, 5.58; N, 6.97; Found: C, 38.83; H, 6.05; N, 7.34.

Example 3

Preparation of
N-[N'-[2(S)-(2(R)-amino-3-mercaptopropylamino)-
3(S)methylpentyl]1,2,3,4-tetrahydro-3(S)-
isoquinolinecarboxyl]-homoserine lactone (Compound 13) and N-[N'-[2(S)-(2(R)-amino-3-mercaptopropylamino)-
3(S)-methylpentyl]-1,2,3,4-tetrahydro-
3(S)isoquinolinecarboxyl]-homoserine (Compound 14)

Following the methods of example 1, except substituting homoserine lactone hydrochloride for methionine methyl ester hydrochloride in Step D, N-[N'-[2(S)-(2(R)-amino-3-mercaptopropylamino)-3(S)-methylpentyl]-1,2,3,4-tetrahydro-3(S)isoquinolinecarboxyl]-homoserine lactone was prepared.

Anal. calculated for $C_{23}H_{36}N_4O_3S \cdot 3CF_3CO_2H$: C, 44.05; H, 4.97; N, 7.09; Found: C, 43.94; H, 5.19; N, 7.13.

N-[N'-[2(S)-(2(R)-amino-3-mercaptopropylamino)-3(S)-methylpentyl]1,2,3,4-tetrahydro-3(S)-isoquinolinecarboxyl]-homoserine was prepared in situ by hydrolyzing the lactone in 1N NaOH/MeOH.

Using the methods described in Examples 1 and 3, but substituting proline or pipecolic acid for 1,2,3,4-tetrahydro-3(S)-isoquinoline carboxylic acid the following compounds were prepared:

N-[2(S)-(2(R)-amino-3-mercaptopropylamino)-3(S)-methylpentyl]-prolyl-homoserine lactone (Compound 15) and N-[2(S)-(2(R)-amino3-mercaptopropylamino)-3(S)-methylpentyl ]-prolyl-homoserine (Compound 16)

Anal. calculated for lactone $C_{18}H_{34}N_4O_3S \cdot 3CF_3CO_2H \cdot 2H_2O$: C, 37.69; H, 5.40; N, 7.33; Found: C, 37.39; H, 4.93; N, 7.47.

N-[2(S)-(2(R)-amino-3-mercaptopropylamino)-3-methylpentyl]-2(S)-pipecolyl-homoserine lactone (Compound 17) and N-[2(S)-(2(R)-amino-3-mercaptopropylamino)-3-methylpentyl ]-2 (S)-pipecolyl-homoserine (Compound 18)

Anal. calculated for lactone $C_{19}H_{36}N_4O_3S \cdot 3CF_3CO_2H \cdot 2H_2O$: C,37.69;H,5.40; N,7.33; Found: C,37.39;H,4.93;N,7.47.

Example 4

Preparation of
N-[2(R)-amino-3-mercaptopropyl]-isoleucyl-prolyl-homserine lactone (Compound 19) and
N-[2(R)-amino-3mercaptopropyl]-isoleucyl-prolyl-homserine (Compound 20)

Step A. t-Butoxycarbonylisoleucine (5.54 g, 0.023 mol), EDC (4.43 g, 0.023 mol), HOOBt (3.77 g, 0.023 mol) and proline benzyl ester hydrochloride (5.0 g, 0.021 mol) were dissolved in $CH_2Cl_2$ (30 mL)-EtOAc (30 mL) with stirring at ambient temperature, the pH was adjusted to 8.5 with diisopropylethylamine (8.04 mL, 0.046 mol) and the mixture stirred for 18 h. The reaction mixture was concentrated, partitioned between EtOAc and $H_2O$, the organic layer separated, washed with 10% citric acid, $H_2O$, aqueous saturated $NaHCO_3$ solution, brine and dried ($Na_2SO_4$). Filtration and concentration to dryness gave the intermediate after chromatography ($SiO_2$, EtOAc: hexane, 1:6 to 1:1.)

Step B. Following the methods of Example 1, steps C through H and Example 3, N-[2(R)-amino-3-mercaptopropyl]-isoleucyl-prolyl-homserine lactone and N-[2(R)-amino-3-mercaptopropyl]-isoleucyl-prolyl-homserine were prepared. Anal. calculated for lactone $C_{18}H_{32}N_4O_4S \cdot 2.5 \ CF_3CO_2H$: C,40.13; H,5.04; N,8.11; Found: C, 39.80; H,5.23; N, 8.45.

N-[2(R)-amino-3-mercaptopropyl]-isoleucyl-2(S)-pipecolyl-homserine lactone (Compound 21) and N-[2(R)-amino-3-mercaptopropyl]-isoleucyl-2(S)-pipecolyl-homserine (Compound 22) were prepared in a similar manner. Anal. calculated for lactone $C_{19}H_{34}N_4O_4S \cdot 3 \ CF_3CO_2H$: C,39.68; H,4.93; N, 7.41; Found: C,39.70; H,5.20; N, 7.56.

Example 5

Preparation of
N-[2(S)-(2(R)-amino-3-(mercaptopropyl)methylamino)3(S)-methylpentyl]-prolyl-methionine methyl ester (Compound 23)

The procedures described in Example 1 were employed with the following changes: proline benzyl ester was substituted for 1,2,3,4-tetrahydro-3(S)-isoquinoline benzyl ester and Step G-1 described below was added after the procedure of Example 1, Step G..

Step G-1. N-[2(S)-(2(R)-(t-butoxycarbonylamino)-3triphenylmethyl mercaptopropylamino)-3(S)-methylpentyl]-prolyl-methionine methyl ester (0.2 g, 0.26 mmol) dissolved in MeOH (2 mL) with stirring under argon was treated with 37% aqueous formaldehyde (0.042 mL, 0.51 mmol), acetic acid (0.015 mL, 0.26 mmol), and sodium cyanoborohydride (0.024 g, 0.39 mmol) at ambient temperature. After 3 h the reaction mixture was concentrated, the residue partitioned between EtOAc (20 mL) and 5% $NH_4OH$ solution (20 mL). The aqueous layer was washed with EtOAc (2×20 mL), the organics combined, washed with brine and dried ($Na_2SO_4$). Filtration and concentration to dryness gave the title compound after chromatography ($SiO_2$, $CH_2Cl_2$: MeOH, 99:1 to 95:5).

Step H. Following Example 1, Step H,N-[2(S)-(2(R)-amino-3-(mercaptopropyl)methylamino)-3(S)-methylpentyl]-prolyl-methionine methyl ester was prepared from N-[2(S)-(2(R)-(t-butoxycarbonylamino)-3-triphenylmethyl mercaptopropylamino)-3(S)-methylpentyl]-prolyl-methionine methyl ester. Anal. calculated for $C_{21}H_{42}N_4O_3S_2 \cdot 2CF_3CO_2H \cdot 1.75 \ H_2O$:C,41.57;H,6.63; N,7.76 ; Found: C,41.59;H,6.28; N,8.12.

Using the methods described in Examples 1, 2 and 5 the following examples were prepared:

N-[2(S)-(2(R)-amino-3-(mercaptopropyl)methylamino)-3(S)-methylpentyl]-prolyl-methionine (Compound 24)

Anal. calculated for $C_{20}H_{40}N_4O_3S_2 \cdot 2.7 \ CF_3CO_2H$: C,40.32; H, 5.69; N, 7.41; Found: C, 40.13; H, 5.28; N, 7.90.

N-[2(S)-(2(R)-amino-3-(mercaptopropyl)methylamino)-3(S)-methylpentyl]-prolyl-methionine sulfone methyl ester (Compound 25)

Anal. calculated for $C_{21}H_{42}N_4O_5S_2 \cdot 4.5 \ HCl$: C,38.28; H,7.11; N, 8.51; Found: C, 38.10; H, 7.34; N, 8.87.

N-[2(S)-(2(R)-amino-3-(mercaptopropyl)methylamino)-3(S)-methylpentyl]-prolyl-methionine sulfone (Compound 26)

Anal. calculated for $C_{20}H_{40}N_4O_5S_2 \cdot 3 \ CF_3CO_2H$: C,37.96; H,5.27; N,6.81; Found: C, 38.22; H, 5.46; N, 7.17.

Example 6

In vitro inhibition of ras farnesyl transferase

Farnesyl-protein transferase (FTase) from bovine brain was chromatographed on DEAE-Sephacel (Pharmacia, 0–0.8 M NaCl gradient elution), N-octyl agarose (Sigma, 0–0.6M NaCl gradient elution), and a mono Q HPLC column (Pharmacia, 0–0.3 M NaCl gradient). Ras-CVLS at 3.5 μM, 0.25 μM [$^3$H]FPP, and the indicated compounds were incubated with either a partially purified bovine enzyme preparation or a recombinant human enzyme preparation. The recombinant human enzyme was prepared as described in Omer, C. A., Kral, A. M., Diehl, R. E., Prendergast, G. C., Powers, S., Allen, C. M., Gibbs, J. B. and Kohl, N. E. (1993) *Biochemistry* 32:5167-5176. The FTase data presented below in Table 1 reflects the ability of the test compound to inhibit RAS farnesylation in vitro, as described in Pompliano, et al., *Biochemistry* 31,3800 (1992).

TABLE I

Inhibition of RAS farnesylation by compounds of this invention*

| Compound | IC$_{50}$ (nM)* |
|---|---|
| 1 | 680 nM |
| 2 | 0.39 nM |
| 3 | 100 nM |
| 4 | 17 nM |
| 5 | 520 nM |
| 6 | 10 nM |
| 7 | 2300 nM |
| 8 | 4.2 nM |
| 9 | 950 nM |
| 10 | 35 nM |
| 11 | 23,000 nM |
| 12 | 7 nM |
| 13 | 390 nM |
| 14 | 7.6 nM |
| 15 | 1400 nM |
| 16 | 45 nM |
| 17 | 24,000 nM |
| 18 | 350 nM |
| 19 | 10,000 nM |
| 20 | 350 nM |
| 21 | 25,000 nM |
| 22 | 340 nM |
| 23 | 1,200 nM |
| 24 | 6 nM |
| 25 | 10,000 nM |
| 26 | 56 nM |

*(IC$_{50}$ is the concentration of the test compound which gives 50% inhibition of FTase under the described assay conditions)

EXAMPLE 7

In vivo ras farnesylation assay

The cell line used in this assay was the v-ras line, which expressed viral Ha-ras p21. The assay was performed essentially as described in DeClue, J. E. et. al., Cancer Research 51, 712-717, (1991). Cells in 10 cm dishes at 50-75% confluency were treated with the test compound (final concentration of solvent, methanol or dimethyl sulfoxide, was 0.1%). After 4 hours at 37° C., the cells were labelled in 3 ml methionine-free DMEM supplemeted with 10% regular DMEM, 2% fetal bovine serum and 400 μCi[$^{35}$S]methionine (1000 Ci/mmol). After an additional 20 hours, the cells were lysed in 1 ml lysis buffer (1% NP40/20 mM HEPES, pH 7.5/5 mM MgCl$_2$/1 mM DTT/10 μg/ml aprotinen/2 μg/ml leupeptin/2 μg/ml antipain/0.5 mM PMSF) and the lysates cleared by centrifugation at 100,000 x g for 45 min. Aliquots of lysates containing equal numbers of acid-precipitable counts were brought to 1 ml with IP buffer (lysis buffer lacking DTT) and immunoprecipitated with the ras-specific monoclonal antibody Y 13-259 (Furth, M. E. et. al., J. Virol. 43,294-304, (1982)). Following a 2 hour antibody incubation at 4° C., 200 μl of a 25% suspension of protein A-Sepharose coated with rabbit anti rat IgG was added for 45 min. The immunoprecipitates were washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein. Data for representative test compounds are tabulated in Table 2.

TABLE 2

Inhibition of Ras Farnesylation by the compounds of this invention in the v-ras cell line

| Compound | IC$_{50}$ (μM)* |
|---|---|
| 1 | 0.25 μM |
| 3 | 0.25 μM |
| 4 | 10 μM |
| 5 | <1 μM |
| 7 | 1 μM |
| 9 | >10 μM |
| 11 | 1 μM |
| 13 | >10 μM |
| 15 | 50 μM |
| 23 | <1 μM |

*<1 = >50% inhibition at a 1 μM concentration

What is claimed is:
1. A compound of the formula I:

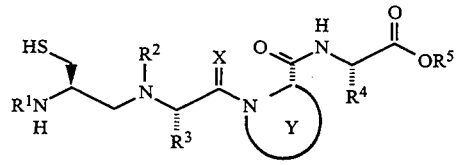

or a pharmaceutically acceptable salt or disulfide thereof; wherein:

R$^1$ and R$^2$ are independently selected from H, C$_{1-4}$ alkyl, C$_{1-4}$ aralkyl, —S(O)$_m$—R$^6$ and

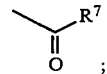

R$^3$ and R$^4$ are independently selected from: H; C$_{1-8}$ alkyl, alkenyl, alkynyl, or

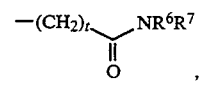

unsubstituted or substituted with one or more of:
1) aryl or heterocycle, unsubstituted or substituted with:
  a. C$_{1-4}$ alkyl,
  b. (CH$_2$)$_t$OR$^6$,
  c. (CH$_2$)$_t$NR$^6$R$^7$, or
  d. halogen,
2) C$_{3-6}$ cycloalkyl,
3) OR$^6$,
4) SR$^6$, S(O)T$^6$, SO$_2$R$^6$, 5) —NR$^6$R$^7$, 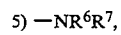

6) 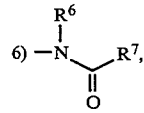

-continued

7) 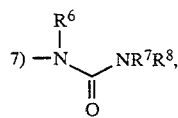

8) 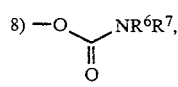

9) 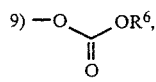

10) 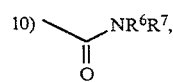

11) 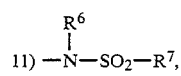

12) 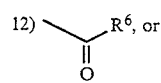

13) 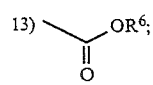

$R^5$ is hydrogen;
$R^6$, $R^7$ and $R^8$ are independently selected from: H; $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e) 

f) $-SO_2R^9$, wherein
$R^6$ and $R^7$ may be joined in a ring, and
$R^7$ and $R^8$ may be joined in a ring;
$R^9$ is $C_{1-4}$ alkyl or aralkyl;
m is 0, 1 or 2;
t is 1 to 4;
X is O or $H_2$; and
Y is substituted or unsubstituted nitrogen containing $C_4$–$C_9$ mono or bicyclic ring system wherein the non-nitrogen containing ring may be an aromatic ring, a $C_5$–$C_7$ saturated ring or a heterocycle and wherein the substituent is selected from $C_{1-4}$ alkyl, $C_{3-6}$ cycloalkyl, heterocycle, aryl, said substituent which is unsubstituted or substituted with:
  a) $C_{1-4}$ alkoxy,
  b) aryl or heterocycle,
  c) halogen,
  d) HO, e) 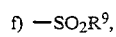

f) $-SO_2R^9$;

provided that Y is not

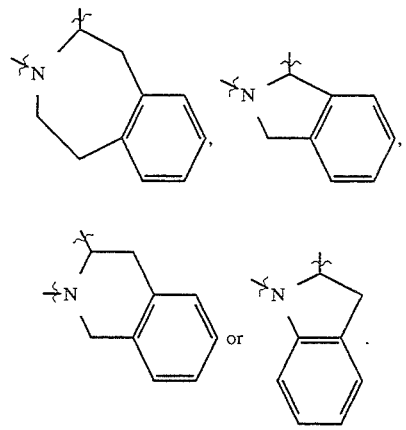

2. A prodrug compound of the formula I:

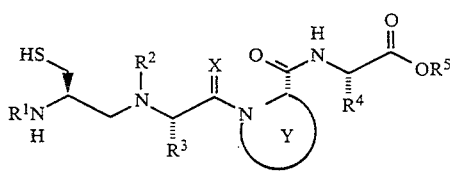

or a pharmaceutically acceptable salt or disulfide thereof; wherein:
$R^1$ and $R^2$ are independently selected from H, $C_{1-4}$ alkyl, $C_{1-4}$ aralkyl, $-S(O)_m-R^6$ and

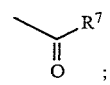

$R^3$ and $R^4$ are independently selected from; H; $C_{1-8}$ alkyl, alkenyl, alkynyl,

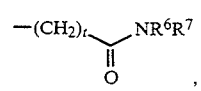

or unsubstituted or substituted with one or more of:
1) aryl or heterocycle, unsubstituted or substituted with:
  a) $C_{1-4}$ alkyl,
  b) $(CH_2)_tOR^6$,
  c) $(CH_2)_tNR^6R^7$,
  d) halogen,
2) $C_{3-6}$ Cycloalkyl,
3) $OR^6$,
4) $SR^6, S(O)R^6, SO_2R^6$,

5) $-NR^6R^7$,

6) 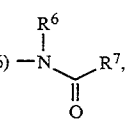

-continued

7) 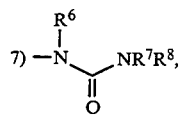

8) 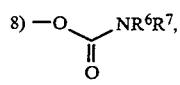

9) 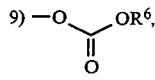

10) 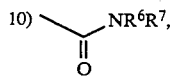

11) 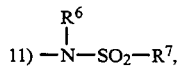

12) 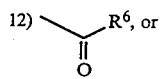

13) 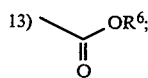

$R^5$ is $C_{1-8}$ alkyl, $C_{3-6}$ cycloalkyl, heterocycle or aryl, unsubstituted or substituted with:
a) $C_{1-4}$ alkoxy,
b) aryl or heterocycle,
c) halogen,
d) HO, e) 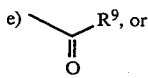

f) $-SO_2R^9$;

e) 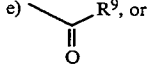

f) $-SO_2R^9$;

provided that Y is not

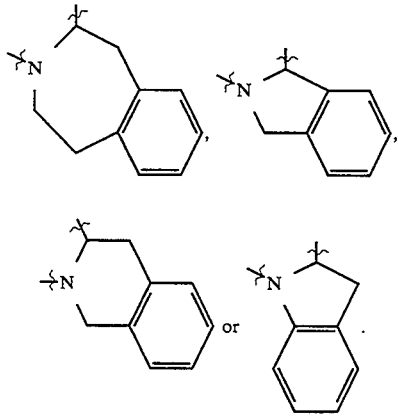

3. The compound according to claim 1 having the formula I:

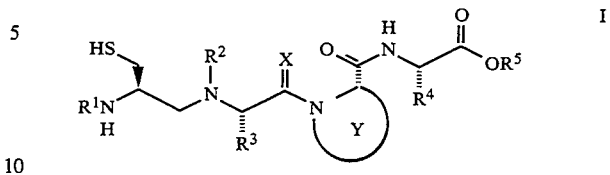

or a pharmaceutically acceptable salt or disulfide thereof; wherein:
$R^1$ and $R^2$ are independently selected from H and $C_{1-4}$ alkyl;
$R^3$ and $R^4$ are independently selected from: H; $C_{1-8}$ alkyl, alkenyl, alkynyl, or

unsubstituted or substituted with one or more of:
1) aryl or heterocycle, unsubstituted or substituted with:
  a) $C_{1-4}$ alkyl,
  b) $(CH_2)_tOR^6$,
  c) $(CH_2)_tNR^6R^7$,
  d) halogen,
2) $C_{3-6}$ cycloalkyl,
3) $OR^6$,
4) $SR^6, S(O)R^6, SO_2R^6$,
$R^5$ is hydrogen;
$R^6$, $R^7$ and $R^8$ are independently selected from: H; $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e) 

f) $-SO_2R^9$, wherein
$R^6$ and $R^7$ may be joined in a ring, and
$R^7$ and $R^8$ may be joined in a ring;
$R^9$ is $C_{1-4}$ alkyl or aralkyl;
m is 0, 1 or 2;
t is 1 to 4;
X is $H_2$; and
Y is substituted or unsubstituted ring system selected from the following

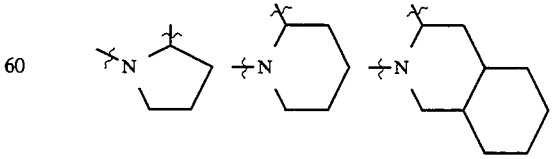

and wherein the substituent is selected from $C_{1-4}$ alkyl, $C_{3-6}$ cycloalkyl, heterocycle, aryl, said substituent which is unsubstituted or substituted with:
a) $C_{1-4}$ alkoxy, b) aryl or heterocycle,
c) halogen,
d) HO,

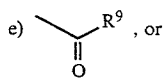

f) —SO$_2$R$^9$.

4. The prodrug compound according to claim 2 having the formula I:

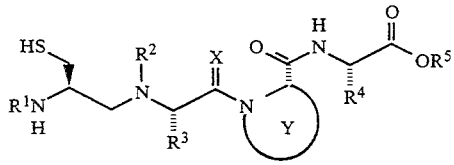

or a pharmaceutically acceptable salt or disulfide thereof; wherein:

R$^1$ and R$^2$ are independently selected from H and C$_{1-4}$ alkyl;

R$^3$ and R$^4$ are independently selected from: H; C$_{1-8}$ alkyl, alkenyl, alkynyl, or

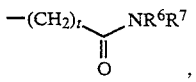

unsubstituted or substituted with one or more of:
1) aryl or heterocycle, unsubstituted or substituted with:
   a) C$_{1-4}$ alkyl,
   b) (CH$_2$)$_t$OR$^6$,
   c) (CH$_2$)$_t$NR$^6$R$^7$,
   d) halogen,
2) C$_{3-6}$ cycloalkyl,
3) OR$^6$,
4) SR$^6$,S(O)R$^6$, SO$_2$R$^6$, R$^5$ is C$_{1-8}$ alkyl, C$_{3-6}$ cycloalkyl, heterocycle or aryl, unsubstituted or substituted with:
   a) C$_{1-4}$ alkoxy,
   b) aryl or heterocycle,
   c) halogen;
   d) HO,

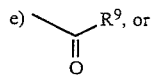

f) —SO$_2$R$^9$;

R$^6$, R$^7$ and R$^8$ are independently selected from: H; C$_{1-4}$ alkyl, C$_{3-6}$ cycloalkyl, heterocycle, aryl, unsubstituted or substituted with:
   a) C$_{1-4}$ alkoxy,
   b) aryl or heterocycle,
   c) halogen,
   d) HO,

f) —SO$_2$R$^9$, wherein
R$^6$ and R$^7$ may be joined in a ring, and
R$^7$ and R$^8$ may be joined in a ring;
R$^9$ is C$_{1-4}$ alkyl or aralkyl;
m is 0, 1 or 2;
t is 1 to 4;
X is H$_2$; and
Y is substituted or unsubstituted ring system selected from the following

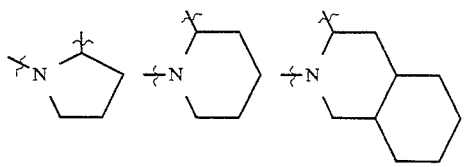

wherein the substituent is selected from C$_{1-4}$ alkyl, C$_{3-6}$ cycloalkyl, heterocycle, aryl, said substituent which is unsubstituted or substituted with:
   a) C$_{1-4}$ alkoxy,
   b) aryl or heterocycle,
   c) halogen,
   d) HO,

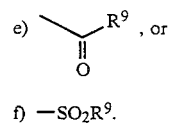

f) —SO$_2$R$^9$.

5. A compound or prodrug compound which is selected from:

N-[2(S)-(2(R)-amino-3-mercaptopropylamino)-3(S)-methylpentyl]-prolyl-methionine methyl ester (Compound 3)

N-[2(S)-(2(R)-amino-3-mercaptopropylamino)-3(S)-methylpentyl]-prolyl-methionine (Compound 4)

N-[2(S)-(2(R)-amino-3-mercaptopropylamino)-3(S)-methylpentyl]-trans-3-ethyl-prolyl-methionine methyl ester (Compound 5)

N-[2(S)-(2(R)-amino-3-mercaptopropylamino)-3(S)-methylpentyl]-trans-3-ethyl-prolyl-methionine (Compound 6)

N-[2(S)-(2(R)-amino-3-mercaptopropylamino)-3(S)-methylpentyl]-cis-3-ethyl-prolyl-methionine methyl ester (compound 7)

N-[2(S)-(2(R)-amino-3-mercaptopropylamino)-3(S)-methylpentyl]-cis-3-ethyl-prolyl-methionine (Compound 8)

N-[2(S)-(2(R)-amino-3-mercaptopropylamino)-3(S)-methylpentyl]-prolyl-methionine sulfone methyl ester (Compound 9)

N-[2(S)-(2(R)-amino-3-mercaptopropylamino)-3(S)-methylpentyl ]-prolyl-methionine sulfone (Compound 10)

N-[2(S)-(2(R)-amino-3-mercaptopropylamino)-3-methylpentyl]-2(S)-pipecolyl-methionine methyl ester (Compound 11 )

N-[2(S)-(2(R)-amino-3-mercaptopropylamino)-3-methylpentyl]-2(S)-pipecolyl-methionine (Compound 12)

N-[2(S)-(2(R)-amino-3-mercaptopropylamino)-3(S)-methylpentyl]-prolyl-homoserine (Compound 16)

N-[2(S)-(2(R)-amino-3-mercaptopropylamino)-3-methylpentyl]-2(S)-pipecolyl-homoserine (Compound 18)

N-[2(R)-amino-3-mercaptopropyl]-isoleucyl-prolyl-homserine (Compound 20)

N-[2(R)-amino-3-mercaptopropyl]-isoleucyl-2(S)-pipecolyl-homserine (Compound 22)

N-[2(S)-(2(R)-amino-3-(mercaptopropyl)methylamino)-3(S)-methylpentyl]-prolyl-methionine methyl ester (Compound 23)

N-[2(S)-(2(R)-amino-3-(mercaptopropyl)methylamino)-3(S)-methylpentyl]-prolyl-methionine (Compound 24)

N-[2(S)-(2(R)-amino-3-(mercaptopropyl)methylamino)-3(S)-methylpentyl]-prolyl-methionine sulfone methyl ester (Compound 25) and N-[2(S)-(2(R)-amino-3-(mercaptopropyl)methylamino)-3(S)-methylpentyl]-prolyl-methionine sulfone (Compound 26)

or a pharmaceutically acceptable salt or disulfide thereof.

6. The compound according to claim 1 which is:
N-[N'-[2(S)-(2(R)-amino-3-mercaptopropylamino)-3(S)-methylpentyl]-1,2,3,4 -tetrahydro-3(S)-isoquinolinecarboxyl]-homoserine (Compound 14)

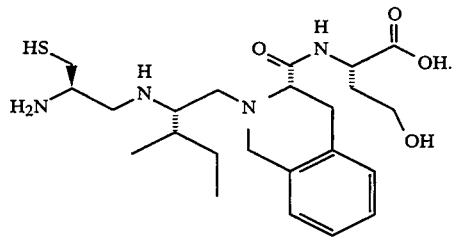

7. The compound according to claim 1 which is:
N-[N'-[2(S)-(2(R)-amino-3-mercaptopropylamino)-3(S)-methylpentyl]-1,2,3,4 -tetrahydro-3(S)-isoquinolinecarboxyl]-methionine (Compound 2)

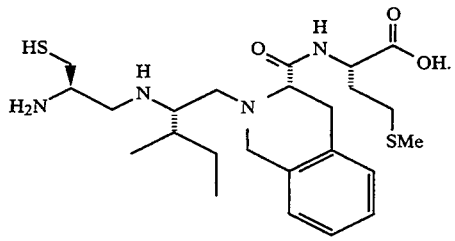

8. The prodrug compound according to claim 2 which is:
N-[N'-[2(S)-(2(R)-amino-3-mercaptopropylamino)-3(S)-methylpentyl]-1,2,3,4 -tetrahydro-3(S)-isoquinolinecarboxyl]-methionine methyl ester (Compound 1)

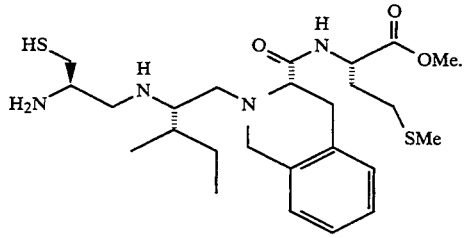

9. The compound according to claim 1 which is:
N-[2(S)-(2(R)-amino-3-mercaptopropylamino)-3(S)-methylpentyl]-trans-3-ethyl-prolyl-methionine (Compound 6)

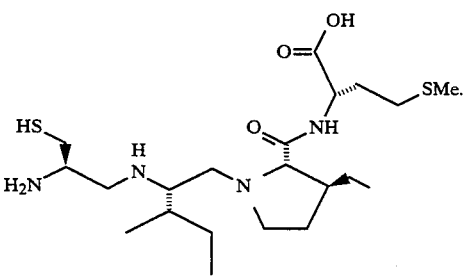

10. The prodrug compound according to claim 0 which is:
N-[2(S)-(2(R)-amino-3-mercaptopropylamino)-3-methylpentyl]-trans-3-ethyl-prolyl-methionine methyl ester (Compound 5)

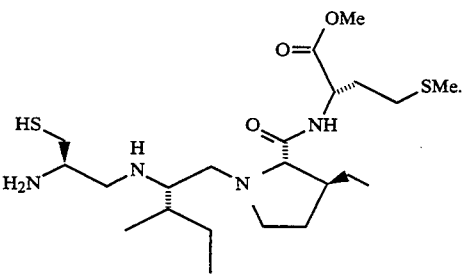

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 3.

13. A pharmaceutical composition comprising a pharmaceutical carrier, and dispersed therein, a therapeutically effective amount of a compound of claim 5.

* * * * *

UNITED STATES PATENT AND TRADEMARK OFFICE
CERTIFICATE OF CORRECTION

PATENT NO. : 5,439,918
DATED : August 8, 1995
INVENTOR(S) : S. Jane deSolms and Samuel L. Graham It is certified that error appears in the above-indentified patent and that said Letters Patent is hereby corrected as shown below:

At Column 28, line 59, replace 4) as follows::

4) $SR^6$, $S(O)R^6$, $SO_2R^6$,

At Column 29, between lines 39-43, replace the structure with the following:

e) 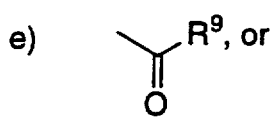, or

At Column 31 at line 43, insert the following text and structures after the phrase "f) - $SO_2R^9$";

$R^6$, $R^7$ and $R^8$ are independently selected from: H; $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO, e) 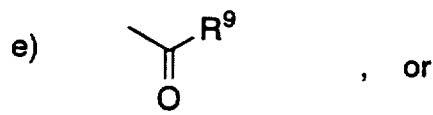 , or f)  , wherein

UNITED STATES PATENT AND TRADEMARK OFFICE
CERTIFICATE OF CORRECTION

PATENT NO. : 5,439,918

DATED : August 8, 1995

INVENTOR(S) : S. Jane deSolms and Samuel L. Graham

It is certified that error appears in the above-indentified patent and that said Letters Patent is hereby corrected as shown below:

$R^6$ and $R^7$ may be joined in a ring, and
$R^7$ and $R^8$ may be joined in a ring;
$R^9$ is $C_{1-4}$ alkyl or aralkyl;

m is 0, 1 or 2;
t is 1 to 4;

X is          O or $H_2$; and

Y is          substituted or unsubstituted nitrogen containing $C_4$-$C_9$ mono or bicyclic ring system wherein the non-nitrogen containing ring may be an aromatic ring, a $C_5$-$C_7$ saturated ring or a heterocycle and wherein the substituent is selected from $C_{1-4}$ alkyl, $C_{3-6}$ cycloalkyl, heterocycle, aryl, said substituent which is unsubstituted or substituted with:

a) $C_{1-4}$ alkoxy, b) aryl or heterocycle, c) halogen, d) HO,

UNITED STATES PATENT AND TRADEMARK OFFICE
CERTIFICATE OF CORRECTION

PATENT NO. : 5,439,918

DATED : August 8, 1995

INVENTOR(S) : S. Jane deSolms and Samuel L. Graham

Page 3 of 4

It is certified that error appears in the above-indentified patent and that said Letters Patent is hereby corrected as shown below:

At Column 32, between lines 43 and 45, replace the structure with the following:

e) 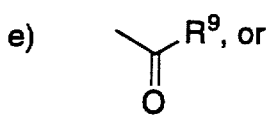

At Column 33, between lines 64-66, replace the structure with the following:

e) 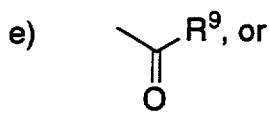

Between Column 35, line 19 and Column 36, line 11, delete Claims 6, 7 and 8.

UNITED STATES PATENT AND TRADEMARK OFFICE
CERTIFICATE OF CORRECTION

PATENT NO. : 5,439,918
DATED : August 8, 1995
INVENTOR(S) : S. Jane deSolms and Samuel L. Graham It is certified that error appears in the above-indentified patent and that said Letters Patent is hereby corrected as shown below:

At Column 36, at line 29, rewrite first line of Claim 10 as follows:

10. The prodrug compound according to Claim 2

Signed and Sealed this

Fifth Day of December, 1995

Attest:

BRUCE LEHMAN

*Attesting Officer*         Commissioner of Patents and Trademarks